United States Patent
Cerf et al.

(10) Patent No.: US 9,345,572 B2
(45) Date of Patent: May 24, 2016

(54) MEDICAL VALVE IMPLANT FOR IMPLANTATION IN AN ANIMAL BODY AND/OR HUMAN BODY

(75) Inventors: Nils Le Cerf, Zollikon (CH); Adalberto Sebastiao Camim, Sao Jose do Rio Preto (BR)

(73) Assignee: BIOTRONIK AG, Buelach (CH)

( * ) Notice: Subject to any disclaimer, the term of this patent is extended or adjusted under 35 U.S.C. 154(b) by 143 days.

(21) Appl. No.: 13/218,147

(22) Filed: Aug. 25, 2011

(65) Prior Publication Data

US 2012/0053685 A1    Mar. 1, 2012

Related U.S. Application Data

(60) Provisional application No. 61/378,420, filed on Aug. 31, 2010.

(51) Int. Cl.
*A61F 2/24* (2006.01)

(52) U.S. Cl.
CPC ........... *A61F 2/2418* (2013.01); *A61F 2/24* (2013.01); *A61F 2230/005* (2013.01); *A61F 2230/008* (2013.01); *A61F 2230/0013* (2013.01)

(58) Field of Classification Search
CPC .......................................... A61F 2/24
USPC ................................. 623/2.1, 2.17
See application file for complete search history.

(56) References Cited

U.S. PATENT DOCUMENTS

| 2004/0039436 A1* | 2/2004 | Spenser et al. ............... 623/1.13 |
| 2005/0096731 A1* | 5/2005 | Looi et al. .................... 623/1.16 |
| 2005/0137686 A1  | 6/2005 | Salahieh et al. |

(Continued)

FOREIGN PATENT DOCUMENTS

| WO | 2009/053497 A1 | 4/2009 |
| WO | 2011/051043 A1 | 5/2011 |

OTHER PUBLICATIONS

Wholey et al. "Designing the Ideal Stent: Stent cell geometry and its clinical significance in carotid stenting" in Endovascular Today, Mar. 2007, pp. 25-34.

(Continued)

*Primary Examiner* — Jacqueline Woznicki
(74) *Attorney, Agent, or Firm* — Wagenknecht IP Law Group PC

(57) ABSTRACT

A medical valve implant (10*a*, 10*b*) for implantation in an animal body and/or human body, comprising a base body (12*a*, 12*b*) that includes a collar (16*a*, 16*b*) extending in circumferential direction (14*a*, 14*b*), wherein the collar (16*a*, 16*b*) includes at least one first cell structure (18*a*, 18*b*) which is provided to form, in the intended end state, an intended inner cross section (24*a*, 24*b*) of base body (12*a*, 12*b*) that is matched to an intended outer cross section (20*a*, 20*b*) of an implant structure (22*a*, 22*b*). It is provided that the collar (16*a*, 16*b*) includes at least one second cell structure (26*a*, 26*b*; 28*a*, 28*b*; 30*a*, 30*b*) that can be moved relative to the at least one cell structure (18*a*, 18*b*), and at least one contact point (32*a*, 32*b*), wherein an outer contour (34*a*, 34*b*) of the base body (12*a*, 12*b*) is formed by the at least one first cell structure (18*a*, 18*b*) and at least the at least one contact point (32*a*, 32*b*) of the at least second cell structure (26*a*, 26*b*; 28*a*, 28*b*; 30*a*, 30*b*), and wherein the at least one contact point (32*a*, 32*b*) forms at least one extreme point (36*a*, 36*b*) of the outer contour (34*a*, 34*b*) relative to a geometric center of gravity (38*a*, 38*b*) of the base body (12*a*, 12*b*).

13 Claims, 6 Drawing Sheets

(56) References Cited

U.S. PATENT DOCUMENTS

| | | | |
|---|---|---|---|
| 2005/0137687 A1* | 6/2005 | Salahieh et al. | 623/2.11 |
| 2007/0255395 A1* | 11/2007 | Pollock | A61F 2/07 623/1.36 |
| 2008/0071361 A1 | 3/2008 | Tuval et al. | |

OTHER PUBLICATIONS

Merriam-Webster definition of "cell" : Merriam-Webster.com, Merriam-Webster n.d. Web. Jan. 3, 2014. <http://www.merriam-webster.com/dictionary/cell>.

* cited by examiner

MEDICAL VALVE IMPLANT FOR IMPLANTATION IN AN ANIMAL BODY AND/OR HUMAN BODY

CROSS REFERENCE TO RELATED APPLICATIONS

This patent application claims the benefit of U.S. Provisional Patent Application No. 61/378,420, filed on Aug. 31, 2010, which is hereby incorporated by reference in its entirety.

TECHNICAL FIELD

The invention relates to a medical valve implant for implantation in an animal body and/or human body.

BACKGROUND

Implants are used in medical applications for implantation in an animal body and/or human body permanently or at least for an extended period of time to perform replacement functions. Valve implants are known, for example, such as aortic valve implants that perform the function of the natural aortic valve.

Methods are known, for example, in which the diseased cusp is clamped between an arm of the implant and the aortic wall and, after the implant structure has been expanded, the valve implant assumes the position of the natural aortic valve. A valve implant of this type in the form of an artificial aortic valve is known e.g. from U.S. Pat. No. 2,926,312. The implant includes elastic structures such as arms and a circular collar which expand to form a circular shape upon implantation, thereby anchoring the implant using its forces that act on the aortic wall.

A problem that occurs frequently with cardiac disease is calcification i.e. the deposition of calcium salts, in particular calcium phosphate (hydroxyapatite), on the structures of the heart. In fact, aortic stenosis that is calcified in a highly asymmetric manner occurs particularly frequently. Implanting a circularly expanding aortic valve implant into a stenosis that has calcified in this manner causes the stent body to deform, resulting in suboptimal functioning of the cusp. This manifests in the form of poorer pressure gradients and a shorter service life of the valve. Furthermore, self-expandable stents show premature signs of fatigue.

SUMMARY

The problem addressed by the invention is that of creating a medical valve implant having improved functionality in cases of strong and/or asymmetrical calcifications at the implantation site.

The invention is directed to a medical valve implant for implantation in an animal body and/or human body, comprising a base body that includes a collar that extends in the circumferential direction, wherein the collar has at least one first cell structure that is designed to form, in the intended end state, an intended inner cross section of the base body that is matched to an intended outer cross section of an implant structure.

It is provided that the collar has at least one second cell structure that is movable relative to the at least first cell structure, and includes at least one contact point, wherein an outer contour of the base body is formed by the at least one first cell structure and at least the at least one contact point of the at least second cell structure, and wherein the at least one contact point forms at least one extreme point of the outer contour relative to a geometric center of gravity of the base body.

A "valve implant" is intended to mean, in particular, a body that functions as a replacement for a non-return valve, permanently or at least for an extended period of time, when implanted in an animal body and/or human body. Other possibilities that are feasible are all medical valve implants that appear suitable to a person skilled in the art, such as an aortic valve, a pulmonary valve, a mitral valve, or a tricuspid valve; particularly advantageously, an embodiment of the medical implant as a stent, in particular a coronary stent, having an implant structure that is connected to the stent in a reversible or irreversible manner is provided. In this context, an "implant structure" is intended to mean, in particular, an aortic valve, a pulmonary valve, a mitral valve, or a tricuspid valve. Another implant structure that appears reasonable to a person skilled in the art would also be feasible, however.

Moreover, the implant structure comprising a valve implant skirt and/or at least one leaflet, which is/are constructed of porcine, bovine, equine and/or other mammalian tissue and/or synthetic material as polyester, PTFE and/or any other material which is feasible for a person skilled in the art. It is a further object of the present invention to provide a valve implant and/or prosthesis that can be implanted trans-femoral, trans-subclavian, trans-apical and/or with any other implantation way, that appears practical to a person skilled in the art. Further, it is possible to use open surgery, minimally invasive techniques percutaneous, and/or associations thereof. Preferably the valve implant is percutaneously-deliverable. Furthermore, it is advantageous to provide a valve implant, especially with a self-expanding stent design, which is manufactured from one piece without joining of different parts that have e.g. three poles with holes for reinforcing the suture of the valve commissural and define geometrically the three leaflets valve design.

Furthermore, a "base body" in this context is intended to mean, in particular, a structure such as a wire mesh that substantially imparts a shape and/or form to the valve implant or, in particular, imparts a shape to the stent, or forms the stent itself. In addition, the base body is preferably composed of an elastic or superelastic material such as a metallic material and/or a combination of a plurality of metallic materials, such as iron, magnesium, nickel, tungsten, titanium, zirconium, niobium, tantalum, zinc, silicon, lithium, sodium, potassium, manganese, and/or any other material that appears reasonable to a person skilled in the art. Another possibility would be a zinc-calcium alloy and/or a material having a memory effect, such as a copper-zinc-aluminum alloy and/or a nickel-titanium alloy, preferably Nitinol. Furthermore, it can be advantageous when the base body includes, at the least, cobalt and/or chromium, preferably in the form of stainless steel and/or a Cr—Ni—Fe steel—preferably the alloy 316L in this case—or a Co—Cr steel. Using this embodiment, an implant can be provided that has good dilatability and advantageous flexibility combined with high stability. Basically, it would also be feasible, however, for the base body of the valve implant to be composed at least partially of plastic, a ceramic, and/or a biodegradable material.

Moreover, it is an object of the present invention to provide a valve implant and/or prosthesis that is a self-expanding implant and permits a self-centering at the implantation site and/or a natural valve annulus after its deployment.

Furthermore, a "collar" in this context is intended to mean a substantially circular structure in particular, which is composed of a netlike or mesh-like wire mesh that extends in a circumferential direction of the stent and in an axial extension of the implant, and is composed largely of similar, recurrent elements or cells of a first cell structure. The main shape of the valve implant or the stent, respectively, is given by any single cell of the base body plus the cells of the first cell structure. In this context, a "first cell structure" is intended to mean a structure or cell shape in particular that dominates the base body or forms at least 50%, preferably at least 60%, and particularly advantageously at least 70% of the base body. Minimal deviations in the shape, such as a curvature of one side of the cell, do not prevent cells from belonging to the cells in the first cell structure. These cells can have any shape that appears suitable to a person skilled in the art, such as round, oval, triangular, rectangular, and/or diamond-shaped. The collar and, therefore, the first cell structure, are used in particular to stabilize the implant or the stent, and to ensure that a radial force of the expanded stent or base body is transferred evenly to an implantation site such as an aortic wall.

In this context, an "intended end state" is intended to mean, in particular, an implanted state of the valve implant in an implantation site such as a site of a defective heart valve. In that case, the implant or the stent is expanded, and is anchored in the correct position at the implantation site. Furthermore, "provided" is intended to mean specially equipped and/or designed.

In this case, an "intended inner cross section of the base body" defines, in particular, an inner cross section of the base body that forms in the implanted state of the stent due to the expansion of the base body or the stent during implantation. The inner cross section of the base body is advantageously a surface of a rotationally symmetrical, preferably round opening that is adapted to an intended outer cross section of the implantation structure or valve, wherein an "intended outer cross section of the implant structure" in this context is intended to mean, in particular, a surface, particularly a circular surface having a maximum extension of the implant in the implanted state substantially perpendicular to a flow direction of a flow medium such as blood. As a result, the implant structure or the valve is accommodated or can be accommodated in the inner cross section with an exact fit.

Furthermore, a "second cell structure" refers, in particular, to a cell structure that deviates from the first cell structure in at least one parameter, such as shape, size, dimension, elasticity, number, and/or another parameter that appears reasonable to a person skilled in the art. Cells in this cell structure can have any shape that appears suitable to a person skilled in the art, such as round, oval, triangular, rectangular, and/or diamond-shaped. At least a portion of the second cell structure is connected to the first cell structure and moves therewith when the valve implant or stent expands.

In this context "movable" is intended to mean, in particular, radially movable and, particularly advantageously, radially movable in the direction of a wall of a blood vessel such as an aortic wall. Preferably, the second cell structure has a lower radial force than a radial force of the first cell structure or the base body, and is preloaded to assume a larger radius than the base body, whereby, in this context, "radial force" is intended to mean, in particular, a force having a vector in the direction of a geometric center or the circle center point of the base body. As a result, when the stent is implanted and therefore expanded, the second cell structure has a greater capability than the first cell structure to move radially outwardly i.e. in the direction of the wall of the blood vessel. The second cell structure or at least a portion of the second cell structure can therefore be moved independently of the first cell structure. This radial difference is independent of a resistance that acts from the outside, such as the force of the wall of the blood vessel (aorta).

Furthermore, a "contact point" refers, in particular, to a point at which at least a portion of the second cell structure has direct contact with the implantation site, such as the annulus and/or a calcification on the annulus or the aortic bulb, after the implantation process. In addition, an "outer contour of the base body" refers to a contour of an outer cross section, wherein the contour is composed of a surface of the first cell structure, which faces the direction of the aortic wall, and the contact points of the first cell structure having e.g. a calcification, and the contact points of the second cell structure with the wall of the blood vessel or the annulus and/or its calcification. Furthermore, the expression "extreme point of the outer contour" refers to a maximum in the extension of the outer cross section, starting from the geometric center of gravity of the base body in the direction of the wall of the blood vessel, whereby the "geometric center of gravity of the base body" refers, in particular, to a center point and, particularly advantageously, a circle center point of the base body.

It is therefore advantageously possible to adjust a variable outer contour of the collar or stent in the implanted state using the second cell structure. Furthermore, the embodiment according to to the invention provides a medical valve implant that is tailored to the parameters or anatomical details of the implantation site, such as a calcification of the blood vessel wall and/or the annulus, and/or another, congenital and/or diseased anomaly of the implantation site. Furthermore, a pressure gradient of the flow medium acting on the medical valve implant can be kept homogeneous, which advantageously results in a minimal material load on the stent and, therefore, in a minimal risk of fatigue, in the case of Nitinol stents in particular, since the stent opens in a uniform manner. This, in turn, results in a long service life of the cusp and, therefore, the valve. Furthermore, better clinical results compared to conventional valve implants can be achieved by the improved functionality of the valve that can therefore withstand a higher pressure gradient in the presence of an asymmetrically calcified annulus. Furthermore, due to the embodiment according to the invention, the symmetry in the flow dynamics of the flow medium can be increased, which advantageously reduces the risk of further calcification.

It is an object of the present invention to provide a percutaneously-deliverable valve implant that with the double cell stent concept manufactured from one piece markedly reduces the delivery profile over known designs.

Moreover, it is provided that at least a portion of the at least second cell structure can be situated obliquely relative to a flow direction of a flow medium. In this context, "oblique" is intended to mean a deviation from the flow direction of the flow medium by up to 45°. At greater angles, the risk of perforation of the aortic wall increases. In this context, a "portion" refers, in particular, to the portion of the second cell structure that can move or move radially relative to the first cell structure. Advantageously, this portion has the shape of a "V", whereby, given the oblique configuration, a tip of the V is situated radially further in the direction of the vessel wall than the part that can be moved with the first cell structure. In this context, a "flow direction of a flow medium" refers, in particular, to the scientifically known flow direction of arterial and/or venous blood in the heart and, particularly advantageously in the case of the aortic valve, to the flow of blood from the left ventricle into the aorta. By realizing the variable oblique position, the implant can be advantageously adapted locally to implantation sites that have changed to different extents and/or that deviate from the round shape of the implantation site.

Advantageously, the at least second cell structure is provided to compensate for a difference in the shape of the inner cross section of the base body and a cross-sectional area of an implantation site. In this context, a "shape of the inner cross section of the base body" refers, in particular, to a largely round or cylindrical shape which enables the cusp of the valve to open and close without complication. A "cross-sectional area of the implantation site" in this context is intended to mean, in particular, a highly asymmetrical or non-circular site, in particular having a calcified aortic stenosis. The second cell structure therefore advantageously adapts the non-uniform shapes of the outer diameter of the valve or the inner cross section of the base body to the cross-sectional area of the implantation site. The cells of the second cell structure have the advantage to adapt to the unknown format and amount of the calcified natural valve varying from its pre shaped form till staying inside the cells of the first cell structure following the shape of the main stent. This variation of the cells of the second cell structure position doesn't interfere with the main shape of the valve implant or stent, respectively. As a result, an asymmetry of the blood vessel wall or the annulus can be compensated for, and a largely round, symmetrical inner shape of the base body can be retained nevertheless to ensure the required flawless, complication-free function of cusps of the valve.

Furthermore, it is advantageous when at least two second cell structures are distributed in the circumferential direction along the collar. Preferably, the second cell structures are distributed evenly, and particularly preferably, three second structures are situated 120° apart from each other. In general, however, any other type of distribution and number would be feasible. The embodiment according to the invention allows the outer contour of the base body to be advantageously adapted, at a plurality of sites, to the local details of the implantation site, and can therefore be used in a particularly variable manner. The position of the cusp suspension relative to the cell structures is not relevant to their function and can be selected in accordance with the actual basic conditions.

In a further embodiment of the invention, the at least second cell structure includes at least one cell group, wherein the at least two cells of one cell group are situated axially one after the other in the flow direction of the flow medium, thereby enabling the outer contour to be adapted to different axially situated details of the implantation site, such as calcifications. This prevents deformation of the base body, which results directly in a rotationally symmetrical or ideal expansion of the stent, which positively affects the function of the cusp in the implanted state. In addition to this effect, the second cell structure likewise results in an anchoring of the implant in the axial direction.

Moreover, it is additionally provided, that the at least second cell structure includes at least one cell with at least two cells halves which are situated in circumferential direction one behind the other, wherein a homogeneous anchoring in circumferential direction can be advantageously achieved.

It is furthermore provided that one cell of the cell group or one cell halve of a cell is situated on an inner contour of a cell of at least the first cell structure. In this context, an "inner contour" refers, in particular, to a contour that points toward a center point of the cell. A cell of the second cell structure is therefore smaller than a cell of the first cell structure. In general, the cell of the cell group could also be situated on another cell structure. Using the configuration according to the invention, the second cell structure can be situated on/in the base body stably and in a space-saving manner.

Furthermore, the cells of the first cell structure can be shaped to facilitate the alignment of the valve prosthesis with the direction of blood flow and to lock the valve implant on the natural valve site improving valve implant fixation on the natural valve annulus. The cells of the second cell structure have the advantage to adapt to the unknown format and amount of the calcified natural valve varying from its pre shaped form till staying inside the cells of the first cell structure following the shape of the main stent. This variation of the cells of the second cell structure position doesn't interfere with the valve implant or stent, respectively, main shape.

Further, providing a valve implant with e.g. a self-expanding stent design that incorporates the first and second cell structures different shapes for the cells of the second cell structure and the cells of the first cell structure can be allowed, wherein interference of one over the other cell types can be minimized when implanted on the natural valve site.

In addition, it is advantageous when a cell of the first and/or second cell structure is substantially diamond-shaped. In this context, the expression "substantially diamond-shaped" is intended to mean, in particular, that shapes that are similar to a diamond or a rhombus, such as a diamond-like shape having rounded corners and/or concave and/or convex sides, can also be referred to as "diamond-shaped". Due to this shape, a particularly stable base body of the implant can be provided.

Advantageously, the cells of the first cell structure and the second cell structure are diamond-shaped, thereby making it possible to situate the second cell structure on the inner contour of the first cell structure using a particularly simple design. Particularly advantageously, the shape of the cell is designed such that it has a mirror axis that is oriented parallel to the flow direction of the flow medium. As a result, the implant can be brought into the state of implantation, that is, the folded-together state, particularly easily.

Furthermore, it can be advantageous for the two cells of a cell group or the two cell halves of a cell to be situated with mirror symmetry relative to each other. This results in axial and/or circumferential anchoring in both possible directions.

A good fixation of the valve and a particularly advantageously stable base body can be achieved when the base body includes a fastening device that is situated between two at least second cell structures and is provided to fix the implant structure in position and stabilize the base body. The fastening device is preferably situated in the center between two second cell structures.

It is also provided that, in the intended end state, the at least second cell structure is situated axially behind an annulus in the flow direction of the flow medium. The annulus is preferably the aortic annulus. The second cell structure can therefore adapt to irregularly calcified aortic cusps.

Particularly advantageously, the medical valve implant is designed as an aortic valve, thereby making it possible to provide a refined replacement structure for the heart valve that malfunctions most often. Favorably, complications such as disruptions of the mitral valve or the need for a cardiac pacemaker can also be reduced. An embodiment as a pulmonary valve or an to embodiment as a mitral valve is likewise feasible.

Advantageously, a deposit-inhibiting, in particular calcification-inhibiting, coating can be provided on the valve implant, in particular homocysteinic acid. The risk of a disruption or malfunction of the valve implant can therefore be reduced.

DESCRIPTION OF THE DRAWINGS

The invention is explained in the following in greater detail, as an example, with reference to an embodiment depicted in drawings. They show.

DETAILED DESCRIPTION

Figure 1:
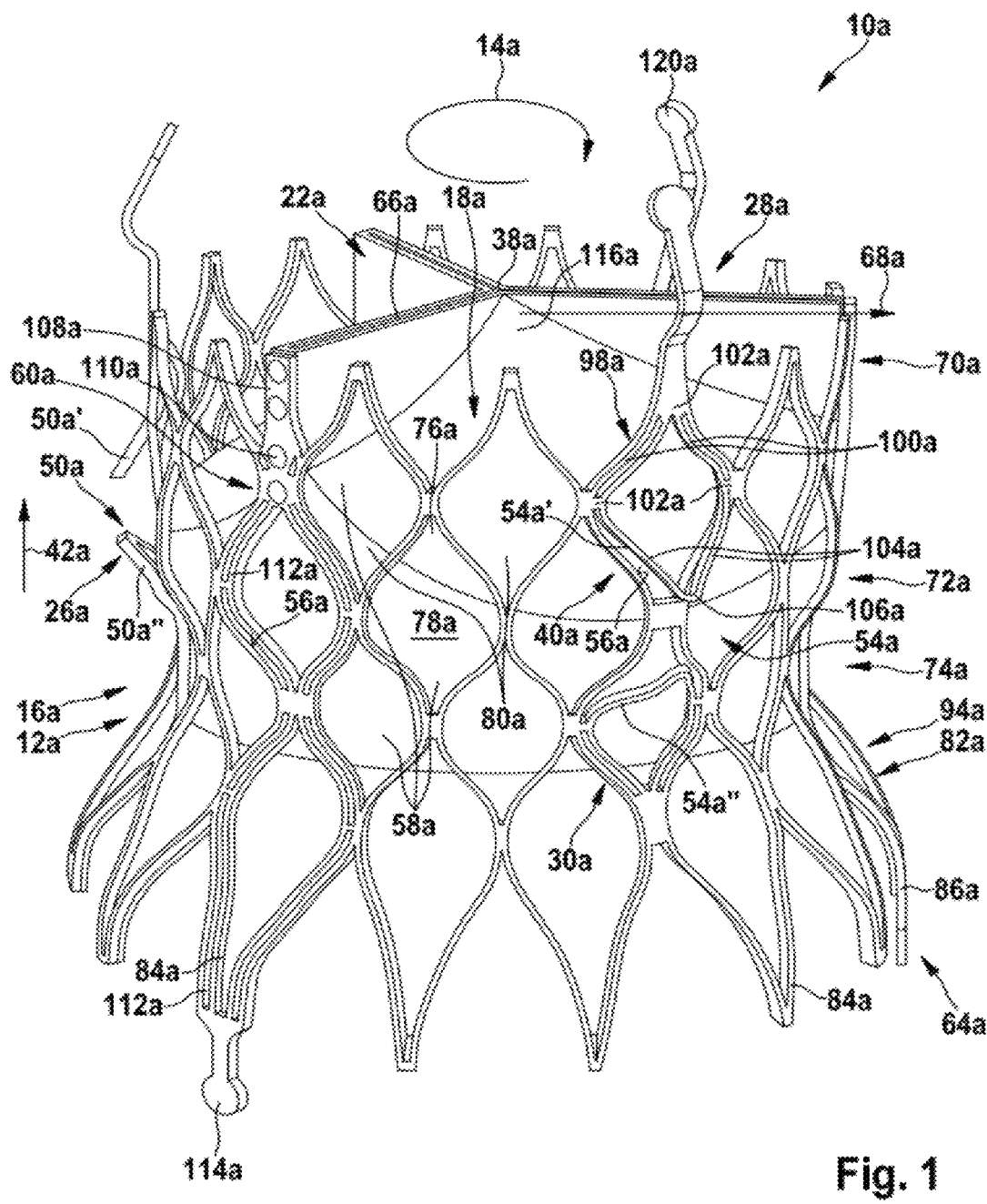
FIG. 1 a medical valve implant according to the invention, in a perspective view, FIG. 2 the valve implant according to FIG. 1, in the implanted state, FIG. 3A a section III-III through the aortic wall including the implanted valve implant according to FIG. 2, FIG. 3B a detailed depiction of the outer contour depicted in FIG. 3a, FIG. 4 a schematic depiction of the insertion of an aortic valve implant at an implantation site and FIG. 5 an alternative embodiment of a valve implant in a perspective view.

Elements that are functionally identical or similar-acting are labeled using the same reference numerals in the figures. The figures are schematic depictions of the invention. They do not depict specific parameters of the invention. Furthermore, the figures merely show typical embodiments of the invention and should not limit the invention to the embodiments shown.

Regarding elements in a figure that are not described further, reference is made to the respective description of the elements in preceding figures to avoid unnecessary repetition.

FIG. 1 shows, in a perspective view, a medical valve implant 10a for implantation in an animal body and/or human body, having a base body 12a which comprises a self-expanding stent 64a and contains an elastic and/or superelastic and/or self-expanding material, in particular Nitinol. Valve implant 10a is furthermore an aortic implant in which an implant structure 22a is fastened to base body 12a or stent 64a, implant structure 22a being designed as an artificial percutaneous aortic valve 66a.

Base body 12a comprises a wire mesh as the base body structure, the wire mesh being formed by a collar 16a that extends in circumferential direction 14a of valve implant 10a. Collar 16a has a first cell structure 18a composed of a large number of cells 58a. Cells 58a are substantially diamond-shaped and are situated next to each other in circumferential direction 14a, and in three rows 70a, 72a, 74a in axial direction. Rows 70a, 72a, 74a are offset in circumferential direction 14a such that—referring to rows 70a and 72a as examples—an upper half 76a, in each case, of a cell 58a of a row 72a is fitted into an intermediate space 78a between two lower halves 80a of cells 58a in row 70a. Cells 58a in rows 70a and 74a are situated axially one above the other. First cell structure 18a is provided to form, in the intended end state i.e. the implanted state of valve implant 10a, an intended inner cross section 24a of base body 12a that is matched to an intended outer cross section 20a of implant structure 22a (see FIG. 3a).

In addition, a further row 82a of end cells 84a adjoin first cell structure 18a of collar 16a, in the same manner as described for rows 70a and 72a; the diamond shape of row 82a includes an extended end section 86a that extends against a flow direction 42a of a flow medium 44a such as blood. Furthermore, end section 86a bulges in a curved shape outwardly in radial direction 68a, toward a wall 88a of a blood vessel 90a such as aorta 92a in the implanted state, and therefore valve implant 10a has a larger diameter in end region 94a than in the region of collar 16a.

Furthermore, collar 16a or base body 12a of valve implant 10a or stent 64a includes further or three second cell structures 26a, 28a, 30a. Second cell structures 26a, 28a, 30a are distributed in circumferential direction 14a along collar 16a, or they are distributed evenly at 120° intervals. Each second cell structure 26a, 28a, 30a includes a cell group 50a, 52a, 54a, each of which includes two cells 50a', 50a", 52a', 52a", 54a', 54a". Cells 50a', 52a', 54a' are located in row 70a and cells 50a", 52a", 54a" are located in row 74a. Each of the two cells 50a', 50a", 52a', 52a", 54a', 54a" belonging to one cell group 50a, 52a, 54a are situated, in the implanted state of valve implant 10a, axially one behind the other in flow direction 42a of flow medium 44a, that is, from left ventricle 96a to aorta 92a, and with mirror symmetry relative to each other.

Each of the cells 50a', 50a", 52a', 52a", 54a', 54a" of cell group 50a, 52a, 54a is substantially diamond-shaped and is situated on an inner contour 56a of a cell 58a of first cell structure 18a. Therefore, cells 50a', 50a", 52a', 52a", 54a', 54a" are smaller than cells 58a. In addition, each of the cells 50a', 50a", 52a', 52a", 54a', 54a" has a portion 98a that is composed of two sides 100a of the diamond and is connected via three fastening points 102a to cell 58a. When stent 64a expands, portion 98a moves in dependence of stent 64a.

A fastening point is not provided on the tip of the "V" on a further portion 40a of cells 50a', 50a", 52a', 52a", 54a', 54a" which are composed of two further sides 104a of the diamond that form the "V", and is therefore movable independently of the first cell structure 18a, thereby enabling second cell structure 26a, 28a, 30a to move relative to first cell structure 18a or enabling it to move in radial direction 68a. Portion 40a of second cell structure 26a, 28a, 30a can therefore be situated obliquely relative to flow direction 42a of flow medium 44a. In the absence of resistance to portion 40a, portions 40a, 98a of cells 50a', 50a", 52a', 52a", 54a', 54a" can therefore assume an angled orientation relative to each other.

Base body 12a furthermore includes three fastening devices 60a, each having the shape of a segment 108a having fastening holes 110a, to which implant structure 22a or aortic valve 66a is fastened. Segment 108a is an axial extension, which extends in flow direction 42a, on a cell 58a of row 72a of collar 16a. In addition, cell 58a is equipped with a reinforcement 112a on its inner contour 56a. End cell 84a, which is located at the same height, likewise includes a reinforcement 112a and an attachment 114a that extends against flow direction 42a. By way of reinforcements 112a, fastening devices 60a contribute to the stability of base body 12a. Attachment 114a is used to connect base body 12a to a catheter in the implantation procedure in case of a transapical implantation, where the catheter is inserted from below or from the tip of the heart, respectively (not shown).

Each fastening device 60a is situated in circumferential direction 14a in the center between two second cell structures 26a, 28a, 30a, and therefore one cusp tip 116a of a cusp 118a of aortic valve 66a is situated in circumferential direction 14a at a level of second cell structure 26a, 28a, 30a. The three cusp suspensions are located at the level of segment 108a, the lower edge of cusp 118a being located approximately at cusp tip 106a. Cusps 118a are therefore not planar, but rather form a three-dimensional, pyramid-shaped structure. Holding devices 120a of base body 12a or stent 64a for a catheter 122a for inserting valve implant 10a are situated in circumferential direction 14a, and extend in flow direction 42a, at the level of second cell structure 26a, 28a, 30a on cell 58a that has contour 56a.

Cusps 118a of valve implant 10a can be provided with a coating to prevent a deposition of calcium salts and, therefore, to prevent calcification of new cusps 118a.

Figure 2:
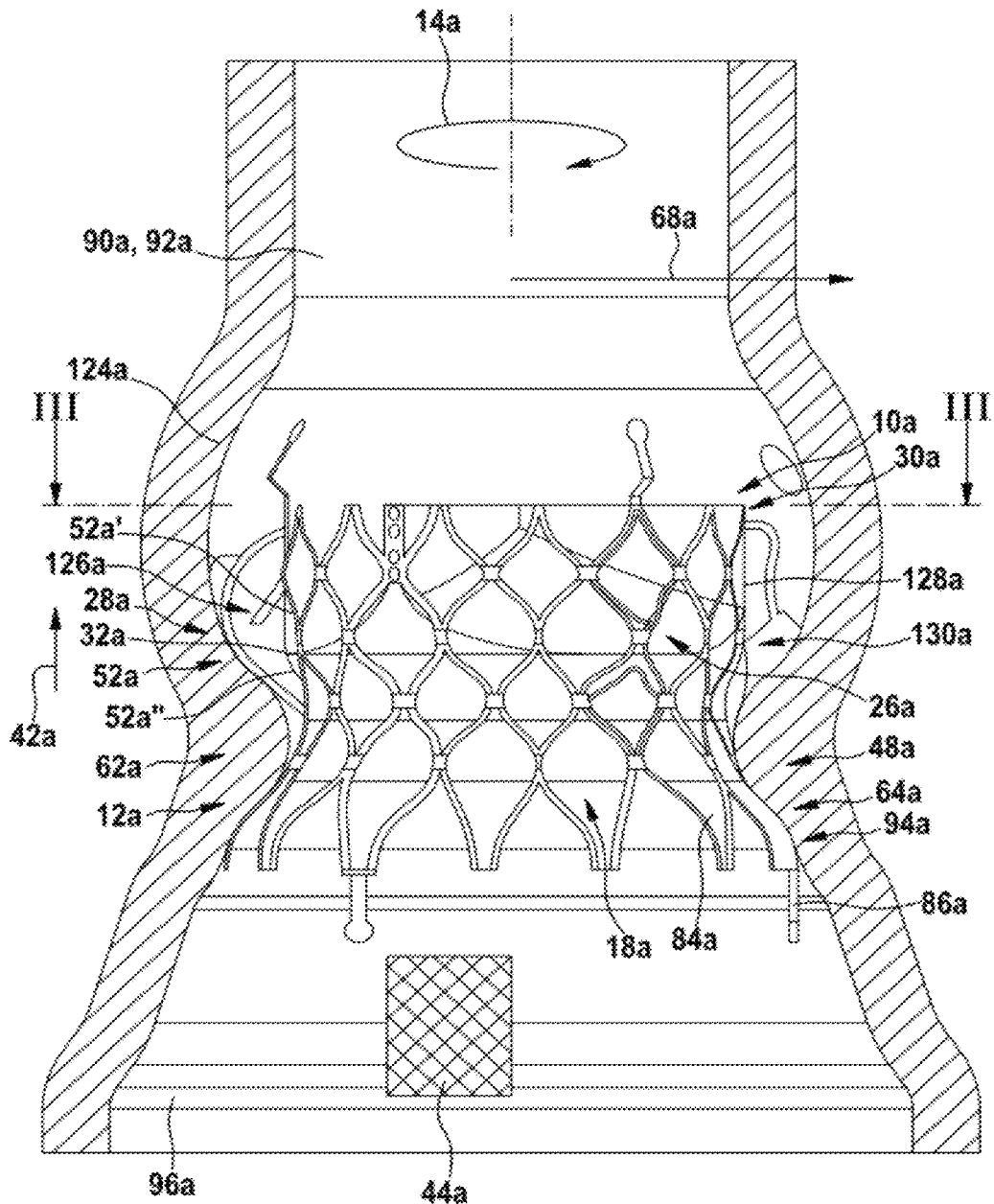

FIG. 2 shows a schematic view of medical valve implant 10a in the implanted state, e.g. in an annulus 62a of a natural aortic valve, that is disposed in blood vessel 90a, which is aorta 92a in this case, in front of left ventricle 96a of the heart. End region 94a, including end section 86a of end cells 84a, which extends further radially outwardly, is situated in front of annulus 62a in flow direction 42a, thereby fixing the broader diameter of end region 94a of stent 64a in position. Furthermore, in the intended end state, second cell structures 26a, 28a, 30a are situated axially behind an annulus 62a, e.g. at the level of an aortic bulb 124a, in flow direction 42a of flow medium 44a, which is indicated only schematically and in regions in FIG. 2.

When the stent 64a is implanted, base body 12a presses the natural aortic valve (see FIG. 4) against a luminal wall 88a of blood vessel 90a, thereby creating open space for implantation structure 22a or artificial aortic valve 66a including cusps 118a in the inner region of base body 12. Natural cusps 118a are pressed upwardly against the vessel wall 88a. Cusps 118a function as non-return valves and permit blood to flow from ventricle 96a to blood vessel 90a, but block the flow of blood in the opposite direction.

When valve implant 10a expands, first cell structure 18a expands, thereby causing end cells 84a of end region 94a to come in contact with wall 88a and fix valve implant 10a in position. A further fixation takes place at two uncalcified regions 126a of the aortic wall in aortic bulb 124a by second cell structure 26a, 28a or portion 40a of cells 50a", 52a" which can move independently of first cell structure 18a further radially outwardly than first cell structure 18a (structures 26a and 50a" are shown only in FIG. 3a, in which cells 50a', 52a' and 54a' were left out to ensure clarity). On a calcified region 128a in aortic bulb 124a, second cell structure 30a expands (indicated schematically in FIG. 3a) only as far as first cell structure 18a since a further expansion of second cell structure 30a or portion 40a is prevented by a calcification 130a in aortic bulb 124a.

Figure 3A:
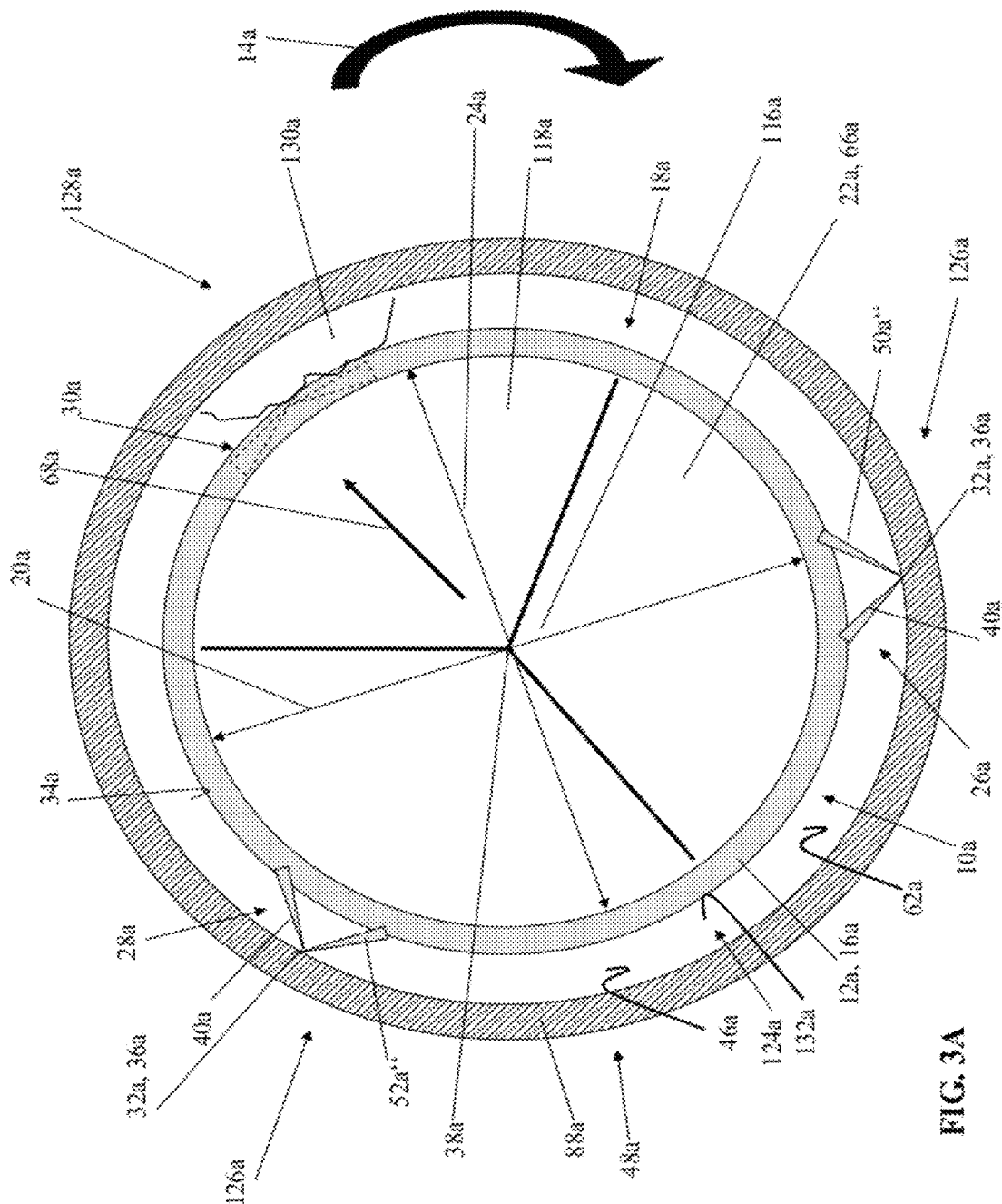
Figure 3B:
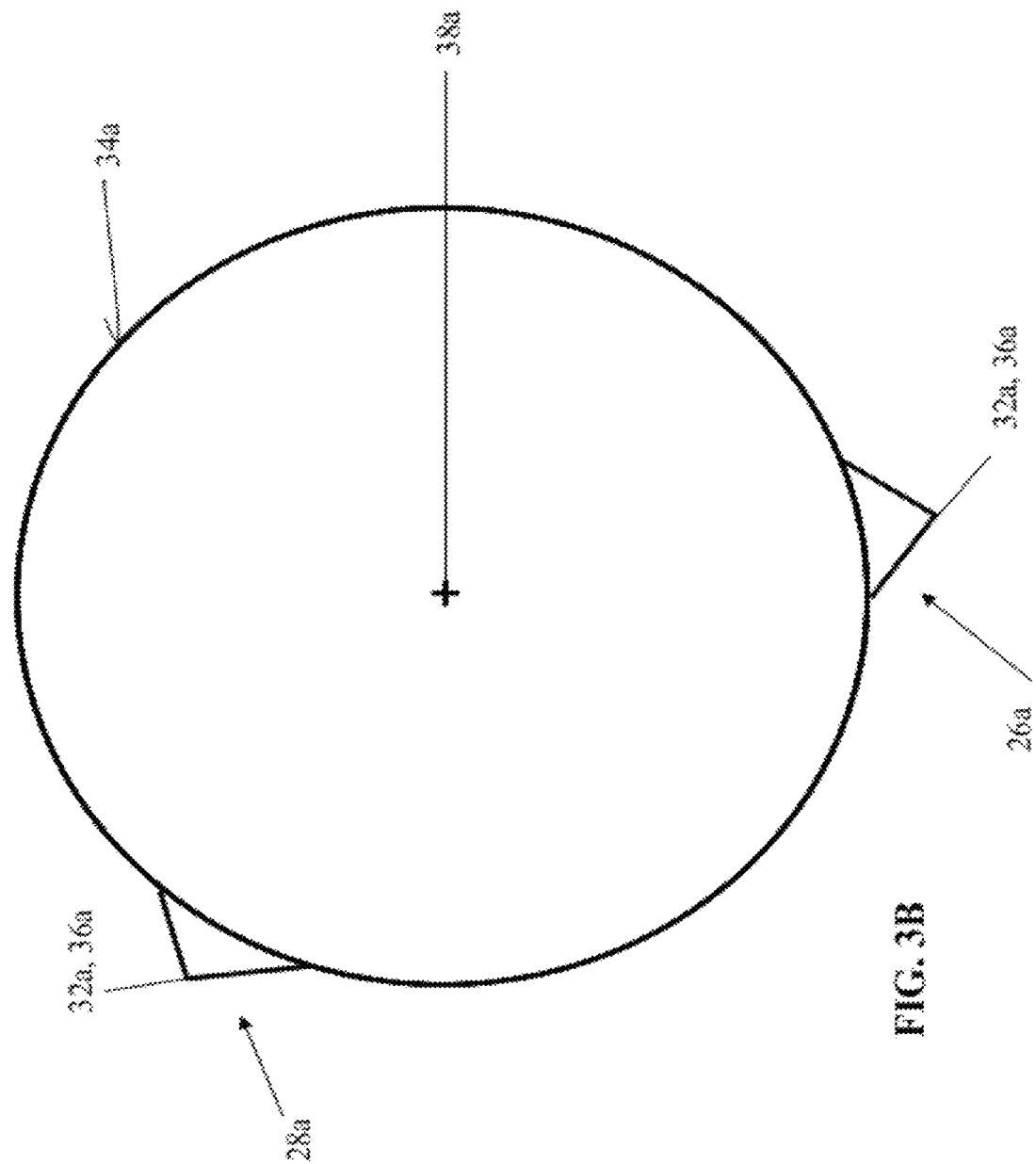

As shown in FIG. 3A, which shows a section III-III through wall 88a of aorta 92a with implanted valve implant 10a according to FIG. 2, second cell structures 26a, 28a each have one contact point 32a. Contact points 32a form outer contour 34a of base body 12a together with a surface 132a, which faces the direction of wall 88a, of first cell structure 18a, and of first and second cell structure 18a, 30a, which adjoin calcification 130a. Outer contour 34a is shown alone in FIG. 3b for clarity. As shown in FIG. 3b, contact points 32a form extreme points 36a of outer contour 34a relative to a geometric center of gravity 38a of base body 12a. Second cell structures 26a, 28a are therefore provided to compensate for a difference in a shape or, in this case, the circular shape of inner cross section 24a of base body 12a and a cross-sectional area 46a of an implantation site 48a.

Figure 4:
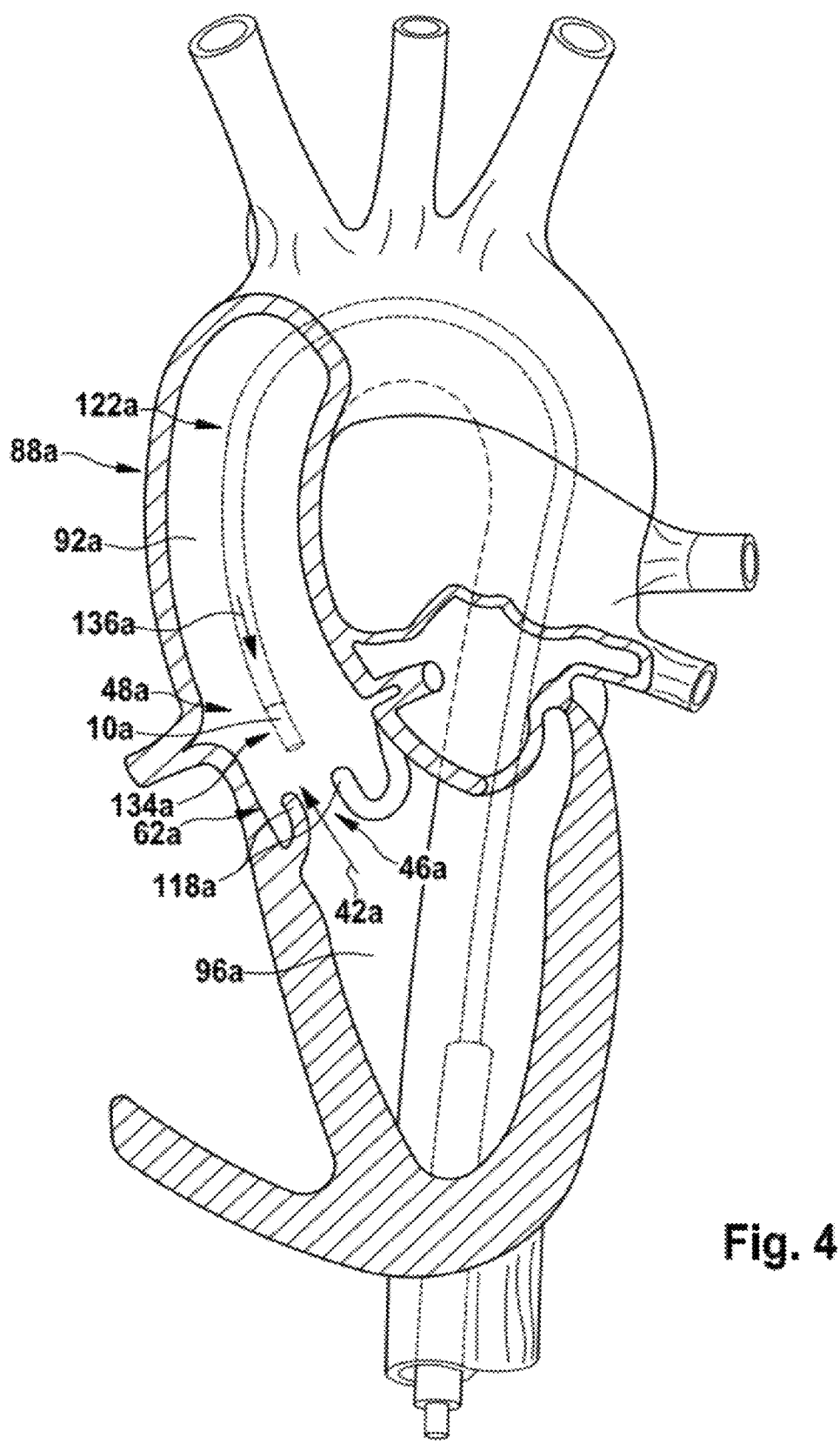

The insertion of medical valve implant 10a is illustrated schematically in a partial sectional view, in FIG. 4. Valve implant 10a is moved, in a compressed state, on a tip 134a of catheter 122a through the aorta 92a in a manner known per se to implantation site 48a e.g. annulus 62a of the natural aortic valve having cusps 118a. In this case, an implantation direction 136a is opposite flow direction 42a. Attachment 114 has no function in the event of this implantation direction 136a.

Figure 5:
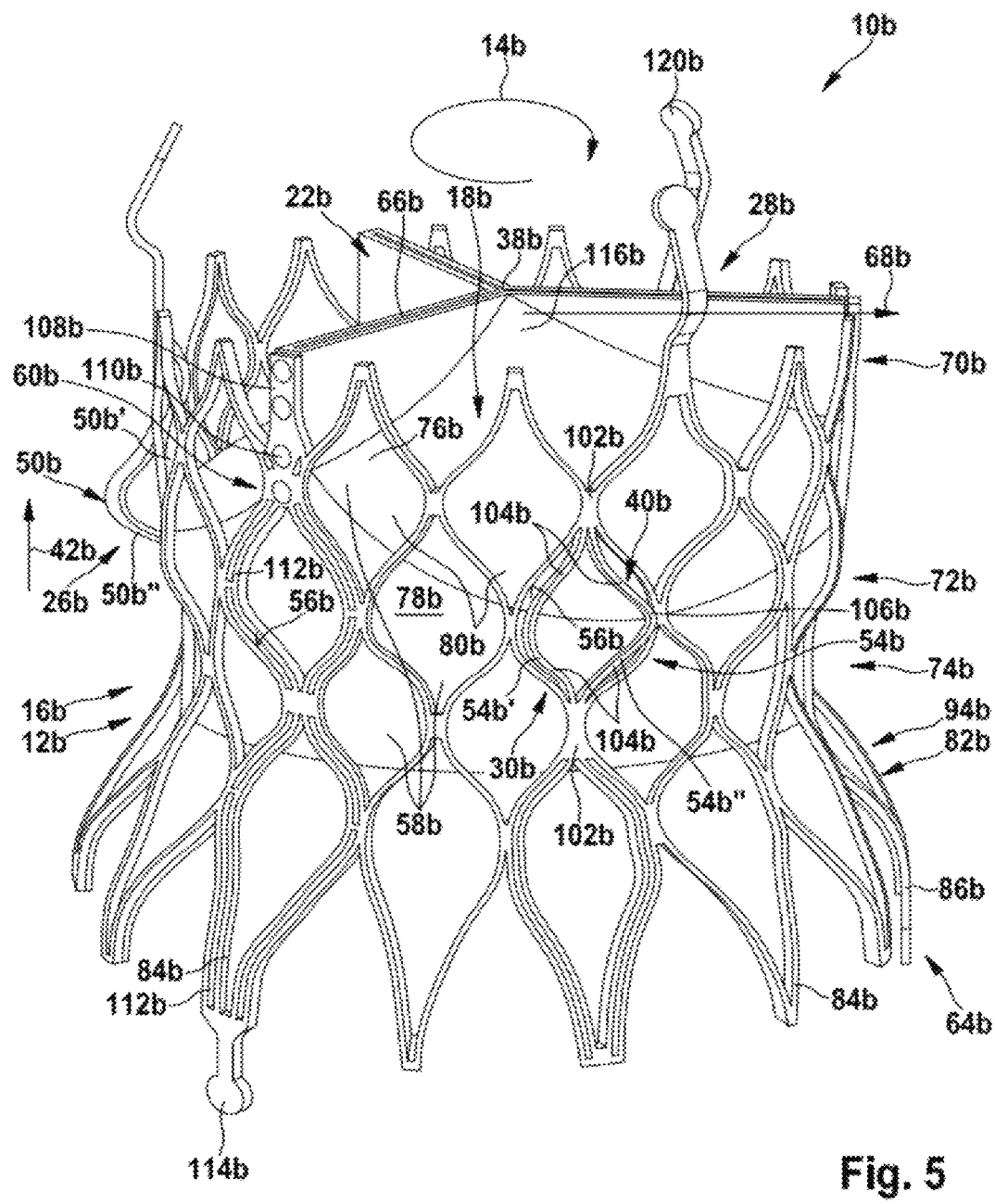

In FIG. 5 an alternative embodiment of the medical valve implant 10a is shown. Components, features and functions that remain identical are in principle substantially denoted by the same reference characters. To distinguish between the two embodiments, however, the letters a and b have been added to the reference characters of the embodiments. The following description is confined substantially to the differences from the embodiment in FIGS. 1 to 4, wherein with regard to components, features and functions that remain identical reference may be made to the description of the embodiment in FIGS. 1 to 4.

FIG. 5 shows, in a perspective view, a medical valve implant 10b for implantation in an animal body and/or human body, having a base body 12b which comprises a self-expanding stent 64b and contains an elastic and/or superelastic and/or self-expanding material, in particular Nitinol. Valve implant 10b is furthermore an aortic implant in which an implant structure 22b is fastened to base body 12b or stent 64b, implant structure 22b being designed as an artificial percutaneous aortic valve 66b.

Base body 12b comprises a wire mesh as the base body structure, the wire mesh being formed by a collar 16b that extends in circumferential direction 14b of valve implant 10b. Collar 16 has a first cell structure 18b composed of a large number of cells 58b. Cells 58b are substantially diamond-shaped and are situated next to each other in circumferential direction 14b, and in three rows 70b, 72b, 74b in axial direction, wherein an upper half 76b, in each case, of a cell 58b of a row 72b is fitted into an intermediate space 78b between two lower halves 80b of cells 58b in row 70b. Cells 58b in rows 70b and 74b are situated axially one above the other. First cell structure 18b is provided to form, in the intended end state i.e. the implanted state of valve implant 10b, an intended inner cross section of base body 12b that is matched to an intended outer cross section of implant structure 22b (not shown, analogous to FIG. 3a).

In addition, a further row 82b of diamond shaped end cells 84b adjoin first cell structure 18b of collar 16b as described above and includes an extended end section 86b that extends against a flow direction 42b of a here not shown flow medium such as blood and bulges in a curved shape outwardly in radial direction 68b, toward a wall of a blood vessel in the implanted state (not shown), and therefore valve implant 10b has a larger diameter in end region 94b than in the region of collar 16b.

Furthermore, collar 16b or base body 12b of valve implant 10b includes further or three second cell structures 26b, 28b, 30b. Second cell structures 26b, 28b, 30b are distributed in circumferential direction 14b along collar 16b, or they are distributed evenly at 120° intervals. Each second cell structure 26b, 28b, 30b includes a cell 50b, 52b, 54b, wherein these cells 50b, 52b, 54b are located in row 72b. Each of the cells 50b, 52b, 54b includes two cell halves 50b', 50b", 52b', 52b", 54b', 54b", wherein each of these two cell halves 50b', 50b", 52b', 52b", 54b', 54b" are situated, in the implanted state of valve implant 10b in circumferential direction 14b one behind the other and with mirror symmetry relative to each other (cell 52b' and cell halves 52b', 52b" are not shown, but embodied identical to cells 50b, 54b or cell halves 50b', 50b", 54b', 54b", respectively).

Each of the cells 50b, 52b, 54b is substantially diamond-shaped and is situated on an inner contour 56b of a cell 58b of first cell structure 18b. Thus, cells 50b, 52b, 54b are smaller than cells 58b. Additionally, each of the cell halves 50b', 50b", 52b', 52b", 54b', 54b" has a portion 40b that is composed of two sides 104b of the diamond and that form a "V". Ends of the sides 104b are each connected via a fastening point 102b to cell 58b. A fastening point is not provided on the tip of the "V" and therefore the portion 40b is movable independently of the first cell structure 18b, thereby enabling second cell structure 26b, 28b, 30b to move relative to first cell structure 18b or enabling it to move in radial direction 68b. Portion 40b of second cell structure 26b, 28b, 30b can therefore be situated obliquely relative to flow direction 42b of the flow medium. In the absence of resistance to portion 40b, portions 40b, of cells 50b, 52b, 54b can therefore assume an angled orientation relative cells 58b.

Base body 12b furthermore includes three fastening devices 60b, wherein each fastening device 60b is situated in circumferential direction 14b between two second cell structures 26b, 28b, 30b. The fastening devices have a segment 108b extending from a cell 58b of row 72b and fastening holes 110*b*, to which the aortic valve 66*b* is fastened. Cell 58*b* and end cell 84*b*, which is located at the same height as cell 58*b* are equipped with a reinforcement 112 on their inner contour 56*b*. End cell 84*b* has an attachment 114*b* to connect base body 12*b* to a catheter in the implantation procedure. Holding devices 120*b* of base body 12*b* for a catheter for inserting valve implant 10*b* are situated in circumferential direction 14*b*, and extend in flow direction 42*b*.

In the case of the here not shown implantation of the stent 64*b* and thus its expansion the cells 50*b*, 52*b*, 54*b* or the portion 40*b* of each cell 50*b*, 52*b*, 54*b*, respectively, has/have the ability to adapt to an unknown format or a cross sectional area of an implantation site in respect to an amount of a calcification at the annulus or the natural valve. This process could vary from its pre shaped form till staying inside the cells 58*b* of the first cell structure 18*b* following the shape of the main stent 64*b* or collar 16*b*, respectively.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A medical valve implant for implantation in an animal body and/or human body, comprising:
an implant structure configured as a medical valve; and
a base body that includes a collar extending in a circumferential direction around the implant structure, wherein the collar includes a first cell structure composed of a plurality of cells, which is provided to form, in an intended end state, an intended inner cross section of the base body that is matched to an intended outer cross section of the implant structure, characterized in that the collar includes at least one group of two cells situated one after the other in a direction of a longitudinal axis of the base body, wherein the two cells within the same group are configured for movement radially outward relative to the first cell structure and in a mirror symmetric fashion to provide at least one contact point, wherein an outer contour of the base body is formed by the first cell structure and the at least one contact point, and wherein the at least one contact point forms at least one extreme point of the outer contour relative to a geometric center of gravity of the base body.

2. The medical valve implant according to claim 1, characterized in that the group of two cells compensates for a difference in a shape of the inner cross section of the base body and a cross-sectional area of an implantation site.

3. The medical valve implant according to claim 1, further comprising two additional groups of two cells characterized in that the groups are distributed 120° from each other in the circumferential direction along the collar.

4. The medical valve implant according to claim 1, characterized in that cells of both the first cell structure and group of two cells are substantially diamond-shaped.

5. The medical valve implant according to claim 1, characterized in that when the two cells of the same group are moved outward relative to the first cell structure, the two cells of the same group are situated with mirror symmetry relative to each other along a plane that is perpendicular to the longitudinal direction of the medical valve implant and that separates the two cells from one another.

6. The medical valve implant according to claim 1, characterized in that the base body includes a fastening device that is situated between two groups of cells and is provided to fix the implant structure in position and stabilize the base body.

7. The medical valve implant according to claim 1, characterized in that the at least one group of two cells is situated axially behind an annulus in a flow direction of a flow medium when implanted.

8. The medical valve implant according to claim 1, characterized in that the base body comprises a self-expanding stent.

9. The medical valve implant according to claim 1, characterized in that the base body includes an elastic and/or superelastic material.

10. The medical valve implant according to claim 1, wherein the medical valve is an aortic valve.

11. The medical valve implant according to claim 1, wherein the medical valve is selected from the group consisting of a pulmonary valve, a mitral valve, and a tricuspid valve.

12. A medical valve implant for implantation in an animal body and/or human body, comprising:
an implant structure configured as a medical valve; and
a collar comprising a plurality of diamond shaped cells joined to form an open mesh extending in a circumferential direction around the implant structure, wherein each of two immediately adjacent cells of the plurality of cells aligned in a direction of the longitudinal axis of the medical valve implant has a smaller cell situated within and fastened to an inner contour of a larger surrounding cell, wherein the smaller cells are each characterized as having a diamond shape cell structure, further wherein each smaller cell is configured for outward movement relative to the larger surrounding cell and in mirror symmetric orientation with another of the smaller cells aligned in the direction of the longitudinal axis.

13. The medical valve implant according to claim 12, wherein the smaller cells within the two adjacent cells are fastened at three points around the diamond shape of the smaller cells thereby permitting a free portion to move radially outward.

* * * * *